US008581024B2

(12) United States Patent
Blake et al.

(10) Patent No.: US 8,581,024 B2
(45) Date of Patent: *Nov. 12, 2013

(54) BLUE TRANSGENIC FLUORESCENT ORNAMENTAL FISH

(75) Inventors: Alan Blake, Austin, TX (US); Richard Crockett, Wilton, CT (US); Aidas Nasevicius, Tampa, FL (US)

(73) Assignee: Yorktown Technologies, L.P., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/561,679

(22) Filed: Jul. 30, 2012

(65) Prior Publication Data

US 2012/0317666 A1 Dec. 13, 2012

Related U.S. Application Data

(63) Continuation of application No. 13/396,471, filed on Feb. 14, 2012, now Pat. No. 8,232,451.

(60) Provisional application No. 61/443,070, filed on Feb. 15, 2011.

(51) Int. Cl.
*A01K 67/027* (2006.01)
*C12N 15/00* (2006.01)

(52) U.S. Cl.
USPC ............... 800/20; 800/13; 800/22; 800/25

(58) Field of Classification Search
USPC .......................... 800/20, 13, 22, 25
See application file for complete search history.

(56) References Cited

U.S. PATENT DOCUMENTS

| | | | |
|---|---|---|---|
| 7,135,613 B1 | 11/2006 | Gong et al. | 800/20 |
| 7,355,095 B2 | 4/2008 | Tsai et al. | 800/25 |
| 7,700,825 B2 | 4/2010 | Blake et al. | 800/20 |
| 7,834,239 B2 | 11/2010 | Gong et al. | 800/20 |
| 8,232,451 B1 * | 7/2012 | Blake et al. | 800/20 |
| 2003/0162292 A1 | 8/2003 | Tsai et al. | 435/455 |
| 2004/0117866 A1 | 6/2004 | Tsai | 800/20 |
| 2004/0143864 A1 | 7/2004 | Gong et al. | 800/20 |
| 2005/0198701 A1* | 9/2005 | Lian et al. | 800/20 |
| 2005/0273874 A1 | 12/2005 | Tsai et al. | 800/20 |
| 2008/0052787 A1 | 2/2008 | Gong et al. | 800/20 |
| 2009/0025645 A1* | 1/2009 | Blake et al. | 119/203 |
| 2009/0035788 A1 | 2/2009 | Griesbeck et al. | 435/7.2 |
| 2009/0133138 A1 | 5/2009 | Tsai | 800/20 |
| 2009/0255006 A1 | 10/2009 | Dougan et al. | 800/20 |
| 2010/0037331 A1 | 2/2010 | Blake et al. | 800/20 |
| 2010/0050280 A1 | 2/2010 | Blake et al. | 800/20 |
| 2010/0145889 A1 | 6/2010 | Blake et al. | 705/500 |

FOREIGN PATENT DOCUMENTS

| | | |
|---|---|---|
| EP | 2166107 | 3/2010 |
| WO | WO 00/49150 | 8/2000 |
| WO | WO 2008/022208 | 2/2008 |
| WO | WO 2009/148549 | 10/2009 |

OTHER PUBLICATIONS

Berquand et al., "Analysis of Cytoskeleton-Destabilizing Agents by Optimized Optical Navigation and AFM Force Measurements," *Microscopy Today*, 18:34-37, 2010.
Day et al., "Fluorescent protein tools for studying protein dynamics in living cells: a review," *J. Biomed Opt.*, 3(3):031202, 2008.
Finley et al., "Three-color imaging using fluorescent proteins in living zebrafish embryos," *Biotechniques*, 31(1):66-70; 72, 2001.
Franco et al., "Control of initial endothelial spreading by topographic activation of focal adhesion kinase," *Soft Matter.*, 77:313-7324, 2011.
Gong et al., "Development of transgenic fish for ornamental and bioreactor by strong expression of fluorescent proteins in the skeletal muscle," *Biochem. Biophys. Res. Commun.*, 308(1):58-63, 2003.
Gong et al., "Green fluorescent protein (GFP) transgenic fish and their applications," *Genetica*, 111(1-3):213-25, 2001.
Ju et al., "Recapitulation of fast skeletal muscle development in zebrafish by transgenic expression of GFP under the *mylz2* promoter," *Dev Dyn.*, 227(1):14-26, 2003.
Laranjeira et al., "Glial cells in the mouse enteric nervous system can undergo neurogenesis in response to injury," *J Clin Invest.*, 121(9):3412-24, 2011.
Liu et al., "Development of expression vectors for transgenic fish," *Biotechnology*, 8:1268-1272, 1990.
Liu et al., "Isolation and characterization of beta-actin gene of carp (*Cyprinus carpio*)." *DNA Seq.*, 1(2):125-36, 1990.
Martynov et al., "Alternative cyclization in GFP-like proteins family," *The Journal of Biological Chemistry*, 276(24):21012-21016, 2001.
Nowotschin et al., "Live-imaging fluorescent proteins in mouse embryos: multi-dimensional, multi-spectral perspectives," *Trends in Biotechnology*, 27(5):266-276, 2009.
Parichy et al., "Zebrafish hybrids suggest genetic mechanisms for pigment pattern diversification in *Danio*," *Dev. Genes Evol.*, 211:319-328, 2001.

(Continued)

*Primary Examiner* — Anoop Singh
(74) *Attorney, Agent, or Firm* — Parker Highlander PLLC

(57) ABSTRACT

The present invention relates to transgenic blue ornamental fish, as well as methods of making such fish by in vitro fertilization techniques. Also disclosed are methods of establishing a population of such transgenic fish and methods of providing them to the ornamental fish industry for the purpose of marketing.

11 Claims, No Drawings

(56) References Cited

OTHER PUBLICATIONS

Shcherbo et al., "Bright far-red fluorescent protein for whole-body imaging," *Nature Methods*, 4(9):741-746, 2007.
Shkrob et al., "Far-red fluorescent proteins evolved from a blue chromoprotein from *Actinia equina*," *Biochem. J.*, 392:649-654, 2005.
Stewart, "Go with the glow: fluorescent proteins to light transgenic organisms," *Trends Biotechnol.*, 24(4):155-62, 2006.
Subach et al., "Conversion of red fluorescent protein into a bright blue probe," *Chemistry & Biology*, 15:1116-1124, 2008.
U.S. Appl. No. 13/334,444 entitled "Chimeric Gene Constructs for Generation of Fluorescent Transgenic Ornamental Fish" by Zhiyuan Gong et al., filed Dec. 22, 2011.
Urbani, "Multi-Color approach to track *Salmonella* during infection,", University of Basel, Master's Thesis, pp. 1-35, Oct. 15, 2009.
Wan et al., "Generation of two-color transgenic zebrafish using the green and red fluorescent protein reporter genes gtp and rfp," *Mar Biotechnol (NY)*, 4(2)146-54, 2002.
Zhu et al., "Regulation of the lmo2 promoter during hematopoietic, and vascular development in zebrafish," *Dev. Biol.*, 281(2):256-269, 2005.
Zhu et al., "Use of the DsRed fluorescent reporter in zebrafish," *Methods Cell. Biol.*, 76:3-12, 2004.
Office Action issued in U.S. Appl. No. 13/396,471, dated Mar. 9, 2012.
Notice of Allowance issued in U.S. Appl. No. 13/396,471, Apr. 30, 2012.

\* cited by examiner

BLUE TRANSGENIC FLUORESCENT ORNAMENTAL FISH

This application is a continuation of application Ser. No. 13/396,471 filed Feb. 14, 2012, now U.S. Pat. No. 8,232,451, which claims priority to U.S. Provisional Application No. 61/443,070 filed on Feb. 15, 2011, the entire contents of which are specifically incorporated herein by reference without disclaimer.

BACKGROUND OF THE INVENTION

1. Field of the Invention

This invention relates to transgenic fish, particularly blue transgenic fish.

2. Description of Related Art

Transgenic technology involves the transfer of a foreign gene into a host organism enabling the host to acquire a new and inheritable trait. Transgenic technology has many potential applications. For example, it can be used to introduce a transgene into a fish in order to create new varieties of fish. There are many ways of introducing a foreign gene into fish, including: microinjection (e.g., Zhu et al., 1985; Du et al., 1992), electroporation (Powers et al., 1992), sperm-mediated gene transfer (Khoo et al., 1992; Sin et al., 1993), gene bombardment or gene gun (Zelenin et al., 1991), liposome-mediated gene transfer (Szelei et al., 1994), and the direct injection of DNA into muscle tissue (Xu et al., 1999). The first transgenic fish report was published by Zhu et al., (1985) using a chimeric gene construct consisting of a mouse metallothionein gene promoter and a human growth hormone gene. Most of the early transgenic fish studies have concentrated on growth hormone gene transfer with an aim of generating fast growing fish. While a majority of early attempts used heterologous growth hormone genes and promoters and failed to produce these fish (e.g. Chourrout et al., 1986; Penman et al., 1990; Brem et al., 1988; Gross et al., 1992), enhanced growth of transgenic fish has been demonstrated in several fish species including Atlantic salmon, several species of Pacific salmons, and loach (e.g. Du et al., 1992; Delvin et al., 1994, 1995; Tsai et al., 1995).

The zebrafish, *Danio rerio*, is a model organism for vertebrate developmental biology. As an experimental model, the zebrafish offers several major advantages such as easy availability of eggs and embryos, tissue clarity throughout embryogenesis, external development, short generation time and easy maintenance of both the adult and the young. Transgenic zebrafish have been used as an experimental tool in zebrafish developmental biology. However, for the ornamental fish industry the dark striped pigmentation of the adult zebrafish does not aid in the efficient display of the various colors that are currently available on the market. More recently, Lamason et al. (2005) in their report showed that the Golden zebrafish carry a recessive mutation in the slc24a5 gene, a putative cation exchanger, and have diminished number, size, and density of melanosomes, which are the pigmented organelles of the melanocytes and hence are lightly pigmented as compared to the wild type zebrafish. The availability of such fish having modified pigmentation for transgenesis with fluorescent proteins would result in better products for the ornamental fish industry due to better visualization of the various colors.

Many fluorescent proteins are known in the art and have been used to investigate various cellular processes, including fluorescent proteins exhibiting a green, red, yellow, blue, or purple color. Although transgenic experiments involving fluorescent proteins have provided new markers and reporters for transgenesis, progress in the field of developing and producing ornamental fish that express such proteins has been limited.

SUMMARY OF THE INVENTION

In certain embodiments, the present invention concerns making transgenic fluorescent fish and providing such fish to the ornamental fish industry.

In some embodiments, transgenic fish or methods of making transgenic fish are provided. In certain aspects, the transgenic fish are fertile, transgenic, fluorescent fish. In a particular embodiment, the fish for use with the disclosed constructs and methods is the Golden zebrafish. Zebrafish skin color is determined by pigment cells in their skin, which contain pigment granules called melanosomes (black or brown color), xanthosomes (yellow color), erythrosomes (orange or red color), or iridosomes (iridescent colors, including white color). The number, size, and density of the pigment granules per pigment cell influence the color of the fish skin. Golden zebrafish have diminished number, size, and density of melanosomes and hence have lighter skin when compared to the wild type zebrafish. Golden zebrafish have a mutation in slc24a5 gene, rendering the fish skin lighter or less pigmented (Lamason et al., 2005).

In certain specific embodiments there are provided transgenic zebrafish comprising specific transgenic integration events, referred to herein as transformation events. These fish are of particular interest because, for example, they embody an aesthetically pleasing blue color. Transgenic fish comprising these specific transgenic events may be homozygous or heterozygous (including, for example, hemizygous) for the transformation event. Homozygous fish bred with fish lacking a transformation event will in nearly all cases produce 100% heterozygous offspring. Eggs, sperm, and embryos comprising these specific transgenic events are also included as part of the invention.

In one such embodiment regarding a specific transgenic integration event, a blue transgenic zebrafish is provided comprising chromosomally integrated transgenes, wherein the zebrafish comprises the "Blue zebrafish 1 transformation event," sperm comprising the Blue zebrafish 1 transformation event having been deposited as ECACC accession no. 11012802. The chromosomally integrated transgenes may be present on one integrated expression cassette or two or more integrated expression cassettes. In certain aspects, such a transgenic zebrafish is a fertile, transgenic zebrafish. In more specific aspects, such a zebrafish is a transgenic Golden zebrafish. Such a transgenic zebrafish may be homozygous or heterozygous (including, for example, hemizygous) for the transgenes or integrated expression cassette(s).

Also disclosed are methods of providing a transgenic zebrafish comprising the Blue zebrafish 1 transformation event to the ornamental fish market. In some embodiments, the method comprises obtaining a transgenic zebrafish comprising chromosomally integrated transgenes, wherein the zebrafish comprises the "Blue zebrafish 1 transformation event," sperm comprising the Blue zebrafish 1 transformation event having been deposited as ECACC accession no. 11012802, and distributing the fish to the ornamental fish market. Such fish may be distributed by a grower to a commercial distributor, or such fish may be distributed by a grower or a commercial distributor to a retailer such as, for example, a multi-product retailer having an ornamental fish department.

In some aspects, methods of producing a transgenic zebrafish are provided comprising: (a) obtaining a zebrafish comprising chromosomally integrated transgenes, wherein the zebrafish comprises the "Blue zebrafish 1 transformation event," sperm comprising the Blue zebrafish 1 transformation event having been deposited as ECACC accession no. 11012802; and (b) breeding the obtained zebrafish with a second zebrafish to provide a transgenic zebrafish comprising the Blue zebrafish 1 transformation event. The second zebrafish may be a transgenic or non-transgenic zebrafish.

In further embodiments, also provided are methods of producing a transgenic organism, the method comprising using sperm comprising the Blue zebrafish 1 transformation, such sperm having been deposited as ECACC accession no. 11012802, to produce transgenic offspring. Such offspring may be, for example, a zebrafish, a species of the *Danio* genus, a fish species related to zebrafish, or another fish species. In some aspects, the fish may be produced using in vitro fertilization techniques known in the art or described herein.

As used in this specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Any embodiment of any of the present methods, kits, and compositions may consist of or consist essentially of—rather than comprise/include/contain/have—the described features and/or steps. Thus, in any of the claims, the term "consisting of" or "consisting essentially of" may be substituted for any of the open-ended linking verbs recited above, in order to change the scope of a given claim from what it would otherwise be using the open-ended linking verb.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Transgenic Fish

In some aspects, the invention regards transgenic fish. Methods of making transgenic fish are described in, for example, U.S. Pat. Nos. 7,135,613; 7,700,825; 7,834,239, each of which is incorporated by reference in its entirety.

It is preferred that fish belonging to species and varieties of fish of commercial value, particularly commercial value within the ornamental fish industry, be used. Such fish include but are not limited to catfish, zebrafish, medaka, carp, tilapia, goldfish, tetras, barbs, sharks (family Cyprinidae), angelfish, loach, koi, glassfish, catfish, discus, eel, tetra, goby, gourami, guppy, Xiphophorus, hatchet fish, Molly fish, or pangasius. A particular fish for use in the context of the invention is zebrafish, *Danio rerio*. Zebrafish are increasingly popular ornamental animals and would be of added commercial value in various colors. Zebrafish embryos are easily accessible and nearly transparent. A fish that is of particular use with the disclosed constructs and methods is the Golden Zebrafish. Zebrafish skin color is determined by pigment cells in their skin, which contain pigment granules called melanosomes. The number, size, and density of the melanosomes per pigment cell influence the color of the fish skin. Golden zebrafish have diminished number, size, and density of melanosomes and hence have lighter skin when compared to the wild type zebrafish. Golden zebrafish have a mutation in the slc24a5 gene, which codes for a putative cation exchanger localized to intracellular membrane, thus rendering the fish skin lighter or less pigmented (Lamason et al., 2005).

Fertilization from Frozen Sperm

Fish sperm freezing methods are well-known in the art; see, e.g., Walker and Streisinger (1983) and Draper and Moens (2007), both of which are incorporated herein by reference in their entireties. To obtain transgenic fish disclosed herein, frozen zebrafish sperm may be used to fertilize eggs, as described in Draper and Moens (2007).

Eggs are collected as described in Draper and Moens (2007). Briefly, two females are placed in tricaine solution at 16 mg/100 mL water. After gill movement has slowed, one of the fish is removed and rinsed in water. The fish is placed on a paper towel to dry briefly and then transferred to a small plastic dish. With slightly damp fingers, one finger is placed on the dorsal side of the fish. The eggs are removed by gently pressing on the ventral side of the fish, starting just behind the pectoral fins and moving toward the tail.

The eggs from the female zebrafish are squeezed into a 35 mm plastic Petri dish. The sperm are thawed at 33° C. in a water bath for 8-10 sec. 70 µl room temperature Hanks solution is added to the vial and mixed. The eggs are then immediately added to the vial and gently mixed. The sperm and eggs are activated by adding 750 µl of fish water and mixing. The mixture is incubated for 5 min at room temperature. The dish is then filled with fish water and incubated at 28° C. After 2-3 hrs, fertile embryos are transferred to small dishes where they are further cultured.

Parichy and Johnson, 2001, which is incorporated by reference in its entirety, provides additional examples regarding in vitro fertilization.

The invention further encompasses progeny of a transgenic fish containing the Blue zebrafish 1 integration event, as well as such transgenic fish derived from a transgenic fish egg, sperm cell, embryo, or other cell containing a genomically integrated transgenic construct. "Progeny," as the term is used herein, can result from breeding two transgenic fish of the invention, or from breeding a first transgenic fish of the invention to a second fish that is not a transgenic fish of the invention. In the latter case, the second fish can, for example, be a wild-type fish, a specialized strain of fish, a mutant fish, or another transgenic fish. The hybrid progeny of these matings have the benefits of the transgene for fluorescence combined with the benefits derived from these other lineages.

The simplest way to identify fish containing the Blue zebrafish 1 transformation event is by visual inspection, as the fish in question would be blue colored and immediately distinguishable from non-transgenic fish.

EXAMPLES

Certain embodiments of the invention are further described with reference to the following examples. These examples are intended to be merely illustrative of the invention and are not intended to limit or restrict the scope of the present invention in any way and should not be construed as providing conditions, parameters, reagents, or starting materials that must be utilized exclusively in order to practice the art of the present invention.

Example 1

Blue Transgenic Zebrafish

Transgenic fish exhibiting a blue color are provided. The specific transgenic events embodied in these fish are designated Blue zebrafish 1. Sperm from these fish may be used to fertilize zebrafish eggs and thereby breed transgenic zebrafish that comprise these specific transgenic integration events. Sperm from this line was deposited with the European Collection of Cell Cultures (ECACC), Porton Down, Salisbury, SP4 OJG, United Kingdom, on Jan. 28, 2011, under the provisions of the Budapest Treaty as "Blue zebrafish 1" (accession no. 11012802; cell line ZEBRAFISH 2011.2 BZF001).

The fluorescent transgenic fish have use as ornamental fish in the market. Stably expressing transgenic lines can be developed by breeding a transgenic individual with a wild-type fish, mutant fish, or another transgenic fish. The desired transgenic fish can be distinguished from non-transgenic fish by observing the fish in white light, sunlight, ultraviolet light, blue light, or any other useful lighting condition that allows visualization of the blue color of the transgenic fish.

The fluorescent transgenic fish should also be valuable in the market for scientific research tools because they can be used for embryonic studies such as tracing cell lineage and cell migration. Additionally, these fish can be used to mark cells in genetic mosaic experiments and in fish cancer models.

\* \* \*

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

REFERENCES

The following references, to the extent that they provide exemplary procedural or other details supplementary to those set forth herein, are specifically incorporated herein by reference.

U.S. Pat. No. 7,135,613
U.S. Pat. No. 7,700,825
U.S. Pat. No. 7,834,239
Brem et al., *Aquaculture,* 68:209-219, 1988.
Chourrout et al., *Aquaculture,* 51:143-150, 1986.
Delvin et al., *Nature,* 371:209-210, 1994.
Draper and Moens, In: *The Zebrafish Book,* 5$^{th}$ Ed.; Eugene, University of Oregon Press, 2007.
Du et al., *Bio/Technology,* 10:176-181, 1992.
Gross et al., *Aquaculature,* 103:253-273, 1992.
Khoo et al., *Aquaculture,* 107:1-19, 1992.
Lamason et al., *Science,* 310(5755):1782-1786, 2005.
Penman et al., *Aquaculture,* 85:35-50, 1990.
Powers et al., *Mol. Marine Biol. Biotechnol.,* 1:301-308, 1992.
Sin et al., *Aquaculature,* 117:57-69, 1993.
Szelei et al., *Transgenic Res.,* 3:116-119, 1994.
Tsai et al., *Can. J. Fish Aquat. Sci.,* 52:776-787, 1995.
Walker and Streisinger, *Genetics* 103: 125-136, 1983.
Xu et al., *DNA Cell Biol.,* 18, 85-95, 1999.
Zelenin et al., *FEBS Lett.,* 287(1-2):118-120, 1991.
Zhu et al., *Z. Angew. Ichthyol.,* 1:31-34, 1985.

What is claimed is:

1. A fluorescent progeny fish of a transgenic fluorescent zebrafish that comprises a chromosomally integrated expression cassette encoding a blue fluorescent protein, wherein the zebrafish and progeny both exhibit fluorescence and comprise the Blue zebrafish 1 transformation event, sperm comprising the Blue zebrafish 1 transformation event having been deposited as ECACC accession no. 11012802.

2. The progeny fish of claim 1, further defined as a fertile, transgenic zebrafish.

3. The progeny fish of claim 1, further defined as a transgenic Golden zebrafish.

4. The progeny fish of claim 1, wherein the fish is homozygous for the integrated expression cassette.

5. The progeny fish of claim 1, wherein the fish is heterozygous for the integrated expression cassette.

6. A method of providing a transgenic fish that exhibits a fluorescence to the ornamental fish market, comprising obtaining a transgenic fluorescent progeny fish in accordance with claim 1, and distributing the fish to the ornamental fish market.

7. The method of claim 6, wherein the fish are distributed by a grower to a commercial distributor.

8. The method of claim 6, wherein the fish are distributed by a grower or a commercial distributor to a retailer.

9. The method of claim 8, wherein the retailer is a multi-product retailer having an ornamental fish department.

10. A method of producing a transgenic fish that exhibits a fluorescence comprising:
   (a) obtaining a transgenic fluorescent zebrafish that exhibits a fluorescence and comprises chromosomally integrated expression cassette encoding a blue fluorescent protein, wherein the zebrafish comprises the Blue zebrafish 1 transformation event, sperm comprising the Blue zebrafish 1 transformation event having been deposited as ECACC accession no. 11012802; and
   (b) breeding the obtained zebrafish with a second fish to provide a transgenic fluorescent progeny fish comprising the Blue zebrafish 1 transformation event.

11. The method of claim 10, wherein the second fish is a non-transgenic fish.

\* \* \* \* \*